US007223720B2

(12) United States Patent
Nieendick et al.

(10) Patent No.: US 7,223,720 B2
(45) Date of Patent: May 29, 2007

(54) CLEANING AND CONDITIONING COMPOSITIONS COMPRISING SILICONES AND WAXES

(75) Inventors: Claus Nieendick, Krefeld (DE); Anke Becker, Duesseldorf (DE); Werner Seipel, Hilden (DE)

(73) Assignee: Cognis IP Management GmbH, Duesseldorf (DE)

( * ) Notice: Subject to any disclaimer, the term of this patent is extended or adjusted under 35 U.S.C. 154(b) by 94 days.

(21) Appl. No.: 11/064,872

(22) Filed: Feb. 24, 2005

(65) Prior Publication Data

US 2005/0202985 A1 Sep. 15, 2005

(30) Foreign Application Priority Data

Feb. 24, 2004 (DE) .................. 10 2004 009 426

(51) Int. Cl.
*C11D 1/94* (2006.01)
*C11D 1/72* (2006.01)
*C11D 3/37* (2006.01)
*C11D 9/36* (2006.01)

(52) U.S. Cl. .............. 510/122; 510/119; 510/123; 510/130; 510/128; 510/356; 510/421; 510/434; 510/466; 510/490

(58) Field of Classification Search ........... 510/122, 510/119, 123, 130, 128, 356, 421, 434, 466, 510/490
See application file for complete search history.

(56) References Cited

U.S. PATENT DOCUMENTS

| 6,004,544 | A | | 12/1999 | Schrader et al. |
| 6,162,423 | A | * | 12/2000 | Sebag et al. ............ 424/70.12 |
| 6,228,831 | B1 | * | 5/2001 | Ansmann et al. ........... 510/416 |
| 6,297,203 | B1 | | 10/2001 | Guskey et al. |
| 6,309,628 | B1 | | 10/2001 | Ansmann et al. |
| 6,383,993 | B1 | * | 5/2002 | Maurin et al. ............. 510/119 |
| 6,417,302 | B1 | | 7/2002 | Bohnen |
| 6,451,298 | B1 | * | 9/2002 | Decoster et al. ......... 424/70.12 |
| 6,521,238 | B1 | * | 2/2003 | Muller et al. ............... 424/401 |
| 6,562,772 | B1 | * | 5/2003 | Maurin et al. ............. 510/124 |
| 6,835,700 | B1 | * | 12/2004 | Nieendick et al. ......... 510/119 |
| 2003/0103926 | A1 | * | 6/2003 | Maubru .................. 424/70.12 |
| 2003/0103927 | A1 | * | 6/2003 | Maubru .................. 424/70.12 |
| 2003/0147842 | A1 | * | 8/2003 | Restle et al. ........... 424/70.122 |

FOREIGN PATENT DOCUMENTS

| EP | 0 918 506 B1 | 6/1999 |
| EP | 1 329 215 A2 | 7/2003 |
| FR | 2 802 087 A1 | 6/2001 |
| WO | WO 97/47274 A2 | 12/1997 |
| WO | WO 98/20845 A1 | 5/1998 |
| WO | WO 99/06414 A1 | 2/1999 |
| WO | WO 2004/014326 A1 | 2/2004 |

\* cited by examiner

*Primary Examiner*—Charles Boyer
(74) *Attorney, Agent, or Firm*—John F. Daniels; Jane E. Alexander

(57) ABSTRACT

Compositions, which can be used in cosmetic applications, comprising: (a) at least one wax selected from the group consisting of dialkyl(ene) alkoxy ethers corresponding to formula (I):

$$R^1-(OC_nH_{2n})_x-O-(C_mH_{2m}O)_y-R^2 \qquad (I)$$

in which $R^1$ and $R^2$ independently of one another represent alkyl and/or alkylene groups containing 16 to 36 carbon atoms, n and m independently of one another represent numbers of 2 to 4 and x and y independently of one another represent numbers of 0 to 10, the sum of x and y being a number of 1 to 10; and dialkyl(ene) carbonates corresponding to formula (II):

$$R^3O-CO-OR^4 \qquad (II)$$

in which $R^3$ and $R^4$ independently of one another represent optionally hydroxyfunctionalized alkyl and/or alkenyl groups containing 16 to 36 carbon atoms, and mixtures thereof; (b) at least one silicone; (c) at least one amphoteric and/or zwitterionic surfactant; and (d) at least one cationic polymer.

20 Claims, No Drawings

CLEANING AND CONDITIONING COMPOSITIONS COMPRISING SILICONES AND WAXES

BACKGROUND OF THE INVENTION

It is known that, after washing, hair not only looks dull, it is also very difficult to comb and manage. For this reason, conditioning agents are added to modern shampoos with a view to overcoming these disadvantages. Thus, EP 0 918 506 B1 describes cosmetic preparations containing certain long-chain dialkyl ethers in combination with silicones in conditioning shampoos. WO 97/47274 also relates to cosmetic cleaning preparations which contain a combination of certain long-chain dialkyl ethers or dialkyl carbonates with surfactants and polyols as a pearlizing component. WO 98/20845 also relates to pearlizing concentrates which contain dialkyl ethers in combination with silicones and certain emulsifiers. WO 99/06414 discloses preparations based on alkoxylated dialkyl ethers, surfactants and silicones.

Now, the problem addressed by the present invention was to provide cosmetic preparations for cleaning hair which would greatly reduce combing work after washing and which would condition the hair, but which at the same time would also show a high foaming capacity and good cleaning performance. In addition, insoluble silicones would lend themselves to stable incorporation in the preparations.

SUMMARY OF THE INVENTION

This invention relates to special conditioning cleaning preparations based on silicones and certain waxes for cleaning keratinous fibres. It has been found that cosmetic preparations containing certain waxes, silicones, amphoteric and/or zwitterionic surfactants and cationic polymers reduce the combing work on hair by at least 25%. The combination of these certain waxes, silicones and cationic polymers develops a synergistic effect which reduces combing work to a far greater extent than would have been expected from the effect of the individual components.

Accordingly, the present invention relates to a cosmetic preparation containing:
(a) at least one wax selected from the group consisting of dialkyl(ene) alkoxy ethers corresponding to formula (I):

$$R^1\text{---}(OC_nH_{2n})_x\text{---}O\text{---}(C_mH_{2m}O)_y\text{---}R^2 \quad (I)$$

in which $R^1$ and $R^2$ independently of one another represent alkyl and/or alkylene groups containing 16 to 36 carbon atoms, n and m independently of one another represent numbers of 2 to 4 and x and y independently of one another represent numbers of 0 to 10, the sum of x and y being a number of 1 to 10; and dialkyl(ene) carbonates with linear, branched, saturated or unsaturated alkyl chains containing 16 to 36 carbon atoms and mixtures thereof,
(b) at least one silicone,
(c) at least one amphoteric and/or zwitterionic surfactant and
(d) at least one cationic polymer.

In a particularly preferred embodiment, the cosmetic preparation according to the invention contains
(a) 0.3 to 5% by weight of at least one wax selected from the group consisting of dialkyl(ene) alkoxy ethers corresponding to formula (I):

$$R^1\text{---}(OC_nH_{2n})_x\text{---}O\text{---}(C_mH_{2m}O)_y\text{---}R^2 \quad (I)$$

in which $R^1$ and $R^2$ independently of one another represent alkyl and/or alkylene groups containing 16 to 36 carbon atoms, n and m independently of one another represent numbers of 2 to 4 and x and y independently of one another represent numbers of 0 to 10, the sum of x and y being a number of 1 to 10; and dialkyl(ene) carbonates with linear, branched, saturated or unsaturated alkyl chains containing 16 to 36 carbon atoms and mixtures thereof,
(b) 0.2 to 5% by weight of at least one silicone,
(c) 1 to 50% by weight of at least one amphoteric and/or zwitterionic surfactant and
(d) 0.1 to 1% by weight of at least one cationic polymer.

DETAILED DESCRIPTION OF THE INVENTION

Dialkyl(ene) alkoxy ethers:

The dialkyl(ene) alkoxy ethers according to the invention are compounds corresponding to formula (I):

$$R^1\text{---}(OC_nH_{2n})_x\text{---}O\text{---}(C_mH_{2m}O)_y\text{---}R^2 \quad (I)$$

in which $R^1$ and $R^2$ independently of one another represent alkyl and/or alkylene groups containing 16 to 36 carbon atoms, preferably 18 to 24 carbon atoms, n and m independently of one another represent numbers of 2 to 4 and x and y independently of one another represent numbers of 0 to 10, the sum of x and y being a number of 1 to 10 and preferably a number of 1 to 4. It is pointed out in this connection that the sum of x and y is a mean value because only average degrees of alkoxylation of the alkyl(ene) alkoxy ethers can be determined. The alkyl(ene) alkoxy ethers according to the invention are present in narrow homolog distributions because alkyl(ene) alkoxy ethers of the type mentioned are normally produced by condensation of the corresponding alkoxylated alcohols.

The alkyl(ene) alkoxy ethers according to the invention may be obtained, for example, by alkoxylating, preferably ethoxylating and/or propoxylating, fatty alcohols containing 16 to 36 carbon atoms and preferably 18 to 24 carbon atoms. In a particularly preferred embodiment, the fatty alcohols are ethoxylated. The fatty alcohols may be alkoxylated, for example, by reaction with ethylene oxide and propylene oxide in a random polymerization. However, EO/PO block polymers, for example, may also be produced. Both types of alkoxylated compounds are encompassed by the present invention. The alkoxylation gives a homolog distribution. In a particularly preferred embodiment, alkoxylated fatty alcohols with a narrow homolog distribution are used to produce the alkyl(ene) alkoxy ethers according to the invention. Subsequent acidic or basic condensation of the corresponding alkoxylated fatty alcohols gives the alkyl(ene) alkoxy ethers to be used in accordance with the invention. These include both symmetrical and non-symmetrical alkyl(ene) alkoxy ethers.

Alkyl(ene) alkoxy ethers with particularly advantageous conditioning properties are obtained by condensation of fatty alcohols containing 16 to 36 carbon atoms such as, for example, cetyl alcohol, cetearyl alcohol, stearyl alcohol, isostearyl alcohol, oleyl alcohol, behenyl alcohol and/or erucyl alcohol. By virtue of the high degree of synergistic co-operation with cationic polymers and silicones in very considerably reducing combing work, PEG-4 distearyl ether is particularly preferred.

The preparations according to the invention contain the above-mentioned alkyl(ene) alkoxy ethers in quantities of 0.3 to 5% by weight, preferably in quantities of 0.5 to 2.5% by weight and, in one particularly preferred embodiment, in quantities of 1 to 2% by weight.

Dialkyl(ene) Carbonates

The dialkyl(ene) carbonates according to the invention are compounds corresponding to formula (II):

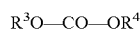
$$R^3O\text{—}CO\text{—}OR^4 \quad (II)$$

in which $R^3$ and $R^4$ independently of one another represent optionally hydroxyfunctionalized alkyl and/or alkenyl groups containing 16 to 36 carbon atoms. These compounds are obtained, for example, by transesterifying dimethyl or diethyl carbonate with the corresponding fatty alcohols or hydroxy alcohols in known manner. Accordingly, the alkyl (ene) carbonates may have a symmetrical or non-symmetrical structure. However, carbonates in which $R^3$ and $R^4$ are the same and represent alkyl groups containing 18 to 24 carbon atoms are preferably used. Transesterification products of dimethyl or diethyl carbonate with cetyl alcohol, cetearyl alcohol, stearyl alcohol, isostearyl alcohol, oleyl alcohol, 12-hydroxystearyl alcohol, behenyl alcohol and/or erucyl alcohol in the form of their mono- and diesters or technical mixtures thereof are particularly preferred.

The preparations according to the invention contain the dialkyl(ene) carbonates in quantities of 0.3 to 5% by weight, preferably in quantities of 0.5 to 2.5% by weight and, in a particularly preferred embodiment, in quantities of 1 to 2% by weight.

Amphoteric or Zwitterionic Surfactants

Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. In a particularly preferred embodiment, the surfactant of component (c) is Cocoamidopropyl Betaine. Ampholytic surfactants are also suitable emulsifiers. Ampholytic surfactants are surface-active compounds which, in addition to an alkyl or acyl group, contain at least one free amino group and at least one —COOH— or —SO$_3$H— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12/13}$ acyl sarcosine.

The preparations according to the invention contain the amphoteric or zwitterionic surfactants in quantities of 1 to 50% by weight, preferably in quantities of 5 to 20% by weight and, in a particularly preferred embodiment, in quantities of 8 to 15% by weight.

Silicones

In the context of the present invention, suitable silicones are polyorganosiloxanes which may be present both in liquid and in resin-like form. The silicones (b) are preferably non-volatile compounds selected from polyalkyl siloxanes, polyaryl siloxanes, polyalkylaryl siloxanes, silicone rubbers and resins and organically modified polyorganosiloxanes and mixtures of these compounds.

The following are mentioned by way of example: trimethylsilyl-terminated polydimethyl siloxanes, dimethylsilanol-terminated polydimethyl siloxanes, poly-($C_{1-20}$)-alkyl siloxanes, polydimethyl siloxane/methyl vinyl siloxanes, polydimethyl siloxane/diphenyl siloxane, polydimethyl siloxane/phenylmethyl siloxane, polydimethyl siloxane/diphenyl siloxane/methyl vinyl siloxanes, mixtures of a terminally hydroxylated polydimethyl siloxane with a cyclic polydimethyl siloxane, mixtures of a polydimethyl siloxane rubber and a cyclic siloxane, mixtures of polydimethyl siloxanes differing in viscosity, linear and/or branched polydimethyl methylphenyl siloxanes and polydimethyl diphenyl siloxanes, silicone rubbers based on polydiorganosiloxanes with a molecular weight of 2,000,000 to 1,000,000 (individually or in a form of a mixture in solvents), chemically modified polyorganosiloxanes containing the following functional groups: polyethyleneoxy and/or polypropyleneoxy groups, optionally substituted amine groups, thiol groups, alkoxy groups, hydroxyalkyl groups and acyloxyalkyl groups.

The above-mentioned silicones are used in the preparations according to the invention in quantities of 0.2 to 5% by weight and preferably in quantities of 0.5 to 2.5% by weight.

Cationic Polymers

The preparations according to the invention contain at least one cationic polymer in a quantity of 0.1 to 1% by weight and, in a particularly preferred embodiment, in a quantity of 0.1 to 0.5% by weight. The cationic polymer is preferably selected from the group of cationically modified polyacrylates, cationically modified polysaccharides, cationically modified polyacrylamides or a mixture of these polymers. Polyquatemium-7, Polyquaternium-10 and cationic guar gum are particularly preferred because, particularly where these polymers are used in the preparations according to the invention, the hair appears extremely soft after washing and a fine-bubble, creamy foam is generated during washing.

EXAMPLES

The following Table shows formulations for Examples of the invention (formulations) and Comparison Examples (formulations).

TABLE 1

Quantities of ingredients in % active substance

| Formulation INCI | 1 | 2 | 3 | 4 | 5 | 6 | 7 | 8 | 9 | 10 | 11 | 12 | 13 |
|---|---|---|---|---|---|---|---|---|---|---|---|---|---|
| Texapon ® N70 Sodium Lauryl Ether Sulphate | 18.6 | 18.6 | 18.6 | 18.6 | 18.6 | 18.6 | 18.6 | 18.6 | 18.6 | 18.6 | 18.6 | 18.6 | 18.6 |
| Dehyton ® PK 45 Cocamidopropylbetaine | 5.0 | 5.0 | 5.0 | 5.0 | 5.0 | 5.0 | — | — | — | 5.0 | 5.0 | 5.0 | 5.0 |
| Dehyton ® AB 40 Coco Betaine | — | — | — | — | — | — | 5.0 | 5.0 | 5.0 | — | — | — | — |
| PEG-4 Distearyl ether | — | — | — | 1.5 | 1.5 | — | — | — | 1.5 | — | 1.5 | 1.5 | — |
| Distearyl carbonate | — | — | — | — | — | 1.5 | 1.5 | — | — | 1.5 | — | — | — |
| Dimethicone (DOW 200) | — | — | 0.75 | 0.75 | 0.75 | 0.75 | 0.75 | 0.75 | 0.75 | 0.75 | — | 0.75 | 0.75 |
| DC 193 PEG-12 Dimethicone | — | — | — | — | 0.5 | — | — | — | — | — | — | — | — |
| Cosmedia ® Guar Guar Hydroxypropyltrimonium Chloride | — | 0.25 | 0.25 | 0.25 | 0.25 | 0.25 | 0.25 | 0.25 | 0.25 | — | 0.25 | — | — |
| Preservative | q.s. | q.s. | q.s. | q.s. | q.s. | q.s. | q.s. | q.s. | q.s. | q.s. | q.s. | q.s. | q.s. |
| Water | to 100 | to 100 | to 100 | to 100 | to 100 | to 100 | to 100 | to 100 | to 100 | to 100 | to 100 | to 100 | to 100 |

Dry and wet combability were determined for Formulations 1 to 13.

In order to determine the combing work, bleached hair tresses were treated (contact time 5 mins) with the product to be tested (1 g product/1 g hair) and then rinsed (tap water, 38° C., 1 l/min.). The forces occurring during combing were then determined in a special measuring apparatus. Combing work was determined by integration from the force/distance curves obtained. The quotient of combing work for untreated hair tresses and the combing work on treated tresses gives the so-called residual combing work. Each measurement was carried out on 20 tresses.

Dry combing work was determined using 18 cm long hair tresses (2 g) which had been conditioned for 12 h in the closed apparatus before the measurement. Combing was carried out with combs having a tooth interval of 2.6 mm. Wet combing work was determined using 15 cm tresses (1 g), the measurements being carried out immediately after rinsing. The combs used had a tooth interval of 0.7 mm. In order to guarantee constant conditions, the entire apparatus was accommodated in a housing where a temperature of 30° C. and a relative air humidity of 40% were maintained.

TABLE 2

| Formulation | Wet combing work before [mJ] | Wet combing work after [mJ] | Residual combing work [%] |
|---|---|---|---|
| 1 | 104.41 | 108.4 | 103.82 |
| 2 | 108.51 | 100.54 | 92.66 |
| 3 | 104.24 | 76.85 | 73.72 |
| 4 | 100.32 | 61.11 | 60.09 |
| 5 | 108.02 | 53.3 | 49.37 |
| 6 | 106.44 | 52.88 | 49.68 |
| 7 | 105.77 | 53.07 | 50.17 |
| 8 | 105.33 | 66.63 | 63.26 |
| 9 | 102.44 | 62.08 | 60.60 |
| 10 | 100.87 | 66.35 | 65.78 |
| 11 | 107.61 | 81.20 | 75.45 |
| 12 | 101.02 | 65.43 | 64.76 |
| 13 | 107.93 | 83.61 | 77.46 |

The measurement results are 95% significantly different in relation to wet combing work before.

TABLE 3

| Formulation | Dry combing work before [mJ] | Dry combing work after [mJ] | Residual combing work [%] |
|---|---|---|---|
| 1 | 55.21 | 52.81 | 95.65 |
| 2 | 49.51 | 41.9 | 84.62 |
| 3 | 56.65 | 37.81 | 66.74 |
| 4 | 57.31 | 24.32 | 42.43 |
| 5 | 54.56 | 17.54 | 32.14 |
| 6 | 48.55 | 21.33 | 43.93 |
| 7 | 52.02 | 24.06 | 46.26 |
| 8 | 57.42 | 36.30 | 63.21 |
| 9 | 54.77 | 23.63 | 43.14 |
| 10 | 52.79 | 26.77 | 50.71 |
| 11 | 56.37 | 42.81 | 75.94 |
| 12 | 49.94 | 24.68 | 49.41 |
| 13 | 56.41 | 42.75 | 75.78 |

The measurement results are 95% significantly different in relation to wet combing work before.

The wet and dry combability results show that the combinations according to the invention of a wax with silicones and cationic polymers produce the greatest reduction in combing work (measurement series 4 to 7 and 9). Comparison of the results of the other measurement series provides a clear illustration of the synergistic effect in relation to the combing work reduction of the combinations of surfactant with polymer (2), surfactant with silicone (13), surfactant with polymer and silicone (3 and 8) by comparison with a composition containing only surfactant. By addition of a wax to a preparation containing cationic polymer and silicone, combing work is again clearly reduced.

What is claimed is:

1. A composition comprising:
   (a) at least one wax component selected from the group consisting of (i) dialkyl(ene) alkoxy ethers corresponding to the general formula (I):

$$R^1-(OC_nH_{2n})_x-O-(C_mH_{2m}O)_y-R^2 \qquad (I)$$

wherein $R^1$ and $R^2$ each independently represent an alkyl or alkylene group having from 16 to 36 carbon atoms, n and m each independently represent a number of from 2 to 4 and x and y each independently represent a number of from 0 to 10, the sum of x and y being a number of from 1 to 10; and (ii) dialkyl(ene) carbonates corresponding to the general formula (II):

$$R^3\text{—O—CO—O}R^4 \qquad (II)$$

wherein $R^3$ and $R^4$ each independently represent an optionally hydroxy-functionalized alkyl or alkenyl group having from 16 to 36 carbon atoms, and mixtures thereof;
(b) at least one silicone;
(c) at least one amphoteric and/or zwitterionic surfactant; and
(d) at least one cationic polymer.

2. The composition according to claim 1, wherein the at least one wax component is present in an amount of from 0.3 to 5% by weight, based on the composition.

3. The composition according to claim 1, wherein the at least one silicone is present in an amount of from 0.2 to 5% by weight, based on the composition.

4. The composition according to claim 1, wherein the at least one amphoteric and/or zwitterionic surfactant is present in an amount of from 1 to 50% by weight, based on the composition.

5. The composition according to claim 1, wherein the at least one cationic polymer is present in an amount of from 0.1 to 1% by weight, based on the composition.

6. The composition according to claim 1, wherein the at least one wax component is present in an amount of from 0.3 to 5% by weight, wherein the at least one silicone is present in an amount of from 0.2 to 5% by weight, wherein the at least one amphoteric and/or zwitterionic surfactant is present in an amount of from 1 to 50% by weight, and wherein the at least one cationic polymer is present in an amount of from 0.1 to 1% by weight, all weights based on the composition.

7. The composition according to claim 1, wherein the at least one amphoteric and/or zwitterionic surfactant comprises cocoamidopropylbetaine.

8. The composition according to claim 4, wherein the at least one amphoteric and/or zwitterionic surfactant comprises cocoamidopropylbetaine.

9. The composition according to claim 6, wherein the at least one amphoteric and/or zwitterionic surfactant comprises cocoamidopropylbetaine.

10. The composition according to claim 1, wherein the at least one cationic polymer comprises a component selected from the group consisting of cationically modified polyacrylates, polysaccharides, polyacrylamides, and mixtures thereof.

11. The composition according to claim 5, wherein the at least one cationic polymer comprises a component selected from the group consisting of cationically modified polyacrylates, polysaccharides, polyacrylamides, and mixtures thereof.

12. The composition according to claim 6, wherein the at least one cationic polymer comprises a component selected from the group consisting of cationically modified polyacrylates, polysaccharides, polyacrylamides, and mixtures thereof.

13. The composition according to claim 1, wherein the at least one silicone comprises a component selected from the group consisting of polyalkyl siloxanes, polyalkylaryl siloxanes, silicone rubbers, silicone resins, organically modified silicones, and mixtures thereof.

14. The composition according to claim 3, wherein the at least one silicone comprises a component selected from the group consisting of polyalkyl siloxanes, polyalkylaryl siloxanes, silicone rubbers, silicone resins, organically modified silicones, and mixtures thereof.

15. The composition according to claim 6, wherein the at least one silicone comprises a component selected from the group consisting of polyalkyl siloxanes, polyalkylaryl siloxanes, silicone rubbers, silicone resins, organically modified silicones, and mixtures thereof.

16. The composition according to claim 1, wherein the at least one wax component comprises a dialkyl(ene) alkoxy ether having a narrow homolog distribution.

17. The composition according to claim 2, wherein the at least one wax component comprises a dialkyl(ene) alkoxy ether having a narrow homolog distribution.

18. The composition according to claim 6, wherein the at least one wax component comprises a dialkyl(ene) alkoxy ether having a narrow homolog distribution.

19. The composition according to claim 6, wherein the at least one wax component comprises a dialkyl(ene) alkoxy ether having a narrow homolog distribution; wherein the at least one silicone comprises a component selected from the group consisting of polyalkyl siloxanes, polyalkylaryl siloxanes, silicone rubbers, silicone resins, organically modified silicones, and mixtures thereof; wherein the at least one amphoteric and/or zwitterionic surfactant comprises cocoamidopropylbetaine; and wherein the at least one cationic polymer comprises a component selected from the group consisting of cationically modified polyacrylates, polysaccharides, polyacrylamides, and mixtures thereof.

20. A composition comprising:
(a) from 0.3 to 5% by weight of at least one wax component selected from the group consisting of (i) dialkyl(ene) alkoxy ethers corresponding to the general formula (I):

$$R^1\text{—}(OC_nH_{2n})_x\text{—O—}(C_mH_{2m}O)_y\text{—}R^2 \qquad (I)$$

wherein $R^1$ and $R^2$ each independently represent an alkyl or alkylene group having from 18 to 24 carbon atoms, n and m each independently represent a number of from 2 to 4 and x and y each independently represent a number of from 0 to 10, the sum of x and y being a number of from 1 to 10; and (ii) dialkyl(ene) carbonates corresponding to the general formula (II):

$$R^3\text{—O—CO—O}R^4 \qquad (II)$$

wherein $R^3$ and $R^4$ each independently represent an optionally hydroxy-functionalized alkyl or alkenyl group having from 18 to 24 carbon atoms, and mixtures thereof;
(b) from 0.2 to 5% by weight of at least one silicone;
(c) from 1 to 50% by weight of at least one amphoteric and/or zwitterionic surfactant; and
(d) from 0.1 to 1% by weight of at least one cationic polymer.

* * * * *